US009351715B2

(12) United States Patent
Mach

(10) Patent No.: US 9,351,715 B2
(45) Date of Patent: May 31, 2016

(54) MULTI-LAYERED MEDICAL DEVICE FOR TREATING A TARGET SITE AND ASSOCIATED METHOD

(75) Inventor: Ryan Mach, Durham, NC (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 818 days.

(21) Appl. No.: 12/179,172

(22) Filed: Jul. 24, 2008

(65) Prior Publication Data

US 2010/0023048 A1 Jan. 28, 2010

(51) Int. Cl.
  *A61B 17/08* (2006.01)
  *A61B 17/00* (2006.01)
  *A61B 17/12* (2006.01)
  *A61M 25/00* (2006.01)

(52) U.S. Cl.
  CPC ....... *A61B 17/0057* (2013.01); *A61B 17/12022* (2013.01); *A61B 17/12109* (2013.01); *A61B 17/12172* (2013.01); *A61B 17/12177* (2013.01); *A61B 2017/00526* (2013.01); *A61B 2017/00893* (2013.01); *A61B 2017/00911* (2013.01); *A61M 25/00* (2013.01); *A61M 25/0026* (2013.01)

(58) Field of Classification Search
  CPC ..................... A61B 17/0057; A61B 17/12109; A61B 17/12177; A61B 17/12022; A61B 17/12172; A61B 2017/00893; A61B 2017/00526; A61B 2017/00911; A61M 25/00; A61M 25/0026
  USPC ........ 606/200, 213; 623/1.11, 1.2, 1, 15, 1.13
  See application file for complete search history.

(56) References Cited

U.S. PATENT DOCUMENTS

| 5,709,713 A | 1/1998 | Evans et al. |
| 5,725,552 A | 3/1998 | Kotula et al. |
| 5,733,294 A | 3/1998 | Forber et al. |
| 5,755,772 A | 5/1998 | Evans et al. |
| 5,846,261 A | 12/1998 | Kotula et al. |
| 5,944,738 A | 8/1999 | Amplatz et al. |
| 6,123,715 A | 9/2000 | Amplatz |

(Continued)

FOREIGN PATENT DOCUMENTS

| JP | 2001515748 | 9/2001 |
| WO | 97/31672 A1 | 9/1997 |
| WO | 2008/151204 A1 | 12/2008 |

OTHER PUBLICATIONS

U.S. Appl. No. 11/966,397, entitled "Percutaneous Catheter Directed Intravascular Occlusion Devices," filed Dec. 28, 2007.

(Continued)

*Primary Examiner* — Jing Ou
(74) *Attorney, Agent, or Firm* — Armstrong Teasdale LLP

(57) ABSTRACT

Embodiments of the present invention provide medical devices and methods for treating a target site within the body, such as for treating vascular abnormalities. For example, one embodiment provides an occlusion device including an occlusive material having proximal and distal ends and a central axis extending therebetween. The occlusive material has a preset, overlapping configuration including at least three inverted overlapping layers folded over one another, wherein the at least three inverted overlapping layers are aligned with the central axis within about 45 degrees or less and are configured to be separated and disposed within a catheter in a non-overlapping configuration and return to the preset, overlapping configuration when deployed from the catheter.

20 Claims, 3 Drawing Sheets

(56) References Cited

U.S. PATENT DOCUMENTS

| | | | |
|---|---|---|---|
| 6,334,864 B1 * | 1/2002 | Amplatz | A61B 17/12022 606/200 |
| 6,355,052 B1 * | 3/2002 | Neuss et al. | 606/213 |
| 6,368,339 B1 | 4/2002 | Amplatz | |
| 6,447,531 B1 | 9/2002 | Amplatz | |
| 6,468,303 B1 * | 10/2002 | Amplatz et al. | 623/1.2 |
| 6,506,204 B2 | 1/2003 | Mazzocchi | |
| 6,579,303 B2 | 6/2003 | Amplatz | |
| 6,599,308 B2 | 7/2003 | Amplatz | |
| 6,797,083 B2 | 9/2004 | Peterson | |
| 6,866,679 B2 | 3/2005 | Kusleika | |
| 7,128,073 B1 * | 10/2006 | van der Burg et al. | 128/887 |
| 7,317,951 B2 * | 1/2008 | Schneider et al. | 607/126 |
| 2003/0032976 A1 | 2/2003 | Boucek | |
| 2005/0155612 A1 | 7/2005 | Matsuura et al. | |
| 2005/0283186 A1 | 12/2005 | Berrada et al. | |
| 2006/0009799 A1 | 1/2006 | Kleshinski et al. | |
| 2006/0135947 A1 | 6/2006 | Soltesz et al. | |
| 2006/0247680 A1 | 11/2006 | Amplatz et al. | |
| 2006/0253181 A1 | 11/2006 | Schulman et al. | |
| 2006/0271166 A1 * | 11/2006 | Thill et al. | 623/1.23 |
| 2007/0043391 A1 * | 2/2007 | Moszner et al. | 606/213 |
| 2007/0112380 A1 | 5/2007 | Figulla et al. | |
| 2007/0118207 A1 | 5/2007 | Amplatz et al. | |
| 2007/0225760 A1 | 9/2007 | Moszner et al. | |
| 2007/0265656 A1 | 11/2007 | Amplatz et al. | |
| 2008/0132996 A1 | 6/2008 | Drasler et al. | |
| 2009/0210047 A1 | 8/2009 | Amplatz et al. | |
| 2010/0023046 A1 | 1/2010 | Heidner et al. | |

OTHER PUBLICATIONS

U.S. Appl. No. 11/827,590, entitled "Percutaneous Catheter Directed Intravascular Occlusion Devices," filed Jul. 12, 2007.

* cited by examiner

MULTI-LAYERED MEDICAL DEVICE FOR TREATING A TARGET SITE AND ASSOCIATED METHOD

BACKGROUND OF THE INVENTION

1) Field of the Invention

The present invention relates to medical devices and, in particular, to a multi-layered device for treating a target site within the body, such as a vascular abnormality.

2) Description of Related Art

Medical devices such as occluders, flow restrictors, shunts, and stent/grafts are known in the art. For example, occlusion devices may be made with a single layer of braided wire fabric to occlude, restrict, or shunt flow through vessels, organs, cavities, or the like. These single-layered devices may be elongated to a reduced diameter for delivery through a catheter and resume their memorized shape when released from the delivery catheter.

Medical devices, such as multi-layered occluders and stent grafts, have also been developed in order to occlude or exclude vascular abnormalities. For example, the medical devices may include multiple layers of coaxially disposed layers of material that are configured to substantially slow the flow of blood and facilitate thrombosis. The idea is that having a greater metallic surface area using a multi-layered device speeds clot formation in comparison to single layer devices and eliminates the need for an additional material such as a polyester fabric often included in single layer devices. If the layers of material are tied together, the layers must elongate the same to be able to be tied at the middle of their longitudinal axis and to be grasped at their ends for loading within a delivery system. If the layers do not elongate the same, one of the layers will be longer than the others in a drawn down configuration, such that some of the layers will be difficult to grasp for delivery. When the layers have the same elongation, the braid geometry is similar between the layers, which can create holes in the device when the layers line up the same. Altering the braid geometry may prevent these gaps, but may lead to differences in elongation, as described above.

Multi-layer devices may be lower in delivery profile than single metal layer devices which incorporate an additional polyester fabric to facilitate occlusion because the metal filaments in a multi-layer device use smaller diameter wire and the multiple layers can all be reduced substantially in diameter together by elongation, where as the polyester fabric must be folded over itself for delivery, causing greater delivery profile in single layer devices. The profile for delivery of multiple layer devices is determined by the additive thickness of each layer in the elongated state. It would be advantageous, if all the benefits of a multi-layer device could be achieved with a lower delivery profile such as by delivering each layer sequentially. A lower delivery profile would provide for a smaller sized delivery catheter, a smaller puncture size into the vasculature, and less trauma to the vascular tissue in passage of the delivery catheter through the vasculature. In addition, smaller catheters are more flexible, and the device may be able to be placed in more difficult to reach anatomical sites such as through smaller diameter vessels or through more tortuous pathways.

Therefore, there is a need for a medical device that is capable of effectively treating various target sites within the body. Moreover, there is a need for a medical device that may be easily delivered and adequately anchored at the target site. In addition, there is a need for a medical device that may be delivered to a target site that is less traumatic to the vasculature and that may be used to prophylactically treat various conditions that may be in more difficult to reach anatomy.

BRIEF SUMMARY OF THE INVENTION

Embodiments of the present invention may provide improvements over the prior art by, among other things, providing medical devices and methods for treating a target site within the body. For example, the medical device may be an occluder for treating various target sites. According to one embodiment of the present invention, an occlusion device for treating a target site is provided and includes an occlusive material having proximal and distal ends and a central axis extending therebetween. The occlusive material has a preset, overlapping configuration including at least three inverted overlapping layers folded over one another, wherein the at least three inverted overlapping layers are aligned with the central axis within about 45 degrees or less and are configured to be separated and disposed within a catheter in a non-overlapping configuration and return to the preset, overlapping configuration when deployed from the catheter.

According to various aspects of the occlusion device, the occlusive material is a continuous layer of fabric. The fabric may be braided strands of a shape memory alloy, wherein each metal strand has a pair of free ends. The occlusion device may include one or more clamps configured to secure a free end of each of the braided metal strands. The at least one clamp may be located distally or proximally with respect to the proximal end or proximally or distally with respect to the distal end in the preset, overlapping configuration. Moreover, the occlusive material may be configured to be axially elongated to separate the at least three inverted overlapping layers into the non-overlapping configuration. The occlusive material may be configured to be constrained to an outer diameter of less than about 11 French for delivery within a catheter in the non-overlapping configuration.

The occlusive material may define a bulbous portion at the proximal and distal ends in the preset, overlapping configuration. In addition, the occlusive material may include a plurality of layers extending perpendicularly to the central axis in the preset, overlapping configuration. The occlusive material may include a disk member at each of the proximal and distal ends in the preset, overlapping configuration, wherein each disk member is oriented perpendicular to the central axis. The occlusive material may include an inner surface and an outer surface in the non-overlapping configuration, wherein at least a portion of the occlusive material may be configured to fold over itself such that a portion of the outer surface overlies another portion of the outer surface. At least one overlapping layer may overlap at least 50% of another overlapping layer. At least one pair of the at least three inverted overlapping layers may be configured to fold greater than about 180 degrees or about 180 degrees or less with respect to one another. At least a pair of the at least three inverted overlapping layers may include surface portions that are configured to be substantially parallel to one another and the central axis in the overlapping configuration. One of the at least three overlapping layers may include a cylindrical outer surface extending parallel to the central axis. Additionally, one of the at least three layers may include a surface extending obliquely with respect to the central axis and within the cylindrical outer surface. The oblique surface could be planar or curved. A portion of the oblique surface may be configured to abut the cylindrical outer surface. The occlusive material may be symmetrical about an axis extending perpendicular to the central axis in the preset, overlapping configuration. Or, the occlusive material may be symmetrical about the central axis in the preset, overlapping configuration.

An additional embodiment of the present invention provides a method for delivering an occlusion device to a target site. The method includes axially elongating an occlusion device having proximal and distal ends and a central axis extending therebetween. The occlusion device has a preset, overlapping configuration including at least three inverted overlapping layers aligned with the central axis within about 45 degrees or less. The elongating step includes elongating the occlusion device such that the at least three overlapping layers are separated into a non-overlapping configuration. The method further includes positioning the occlusion device in the non-overlapping configuration in a catheter, delivering the occlusion device proximate to the target site, and deploying the occlusion device from the catheter such that the occlusion device returns to the overlapping configuration.

According to various aspects of the method, the deploying step includes retracting the catheter to at least partially release the occlusion device. The deploying step may also include deploying the occlusion device such that the occlusion device is configured to self-expand and return to the overlapping configuration when deployed from the catheter. The axially elongating step may include axially elongating the occlusion device to an outer diameter of less than about 11 French. In addition, the axially elongating step may include axially elongating the occlusion device into the non-overlapping configuration having a smaller diameter and a greater length than the overlapping configuration. The delivering step may include delivering the occlusion device over a guide wire.

Another embodiment provides a method of fabricating an occlusion device. The method includes providing an occlusive material braided into a tubular member having a central axis and an initial length. The method further includes manipulating the tubular member to define an overlapping configuration having at least three overlapping layers and a length less than the initial length, wherein the at least three inverted overlapping layers are aligned with the central axis within about 45 degrees or less. Moreover, the method includes positioning the occlusive material on a mandrel and/or within a mold, and heat setting the occlusive material in the overlapping configuration such that the at least three inverted overlapping layers are configured to be separated and disposed within a catheter in a non-overlapping configuration and to return to the preset, overlapping configuration when deployed from the catheter. The method could optionally include clamping at least one free end of the tubular member.

BRIEF DESCRIPTION OF THE SEVERAL VIEWS OF THE DRAWINGS

Figure 1:
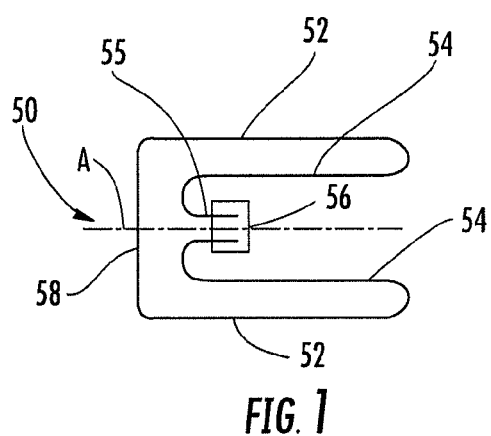

Having thus described the invention in general terms, reference will now be made to the accompanying drawings, which are not necessarily drawn to scale, and wherein:

FIGS. 1-10 illustrate cross-sectional views of occlusion devices according to various embodiments of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as occluding various vascular abnormalities, which may include, for example, occluding an Arterial Venous Malformation (AVM), an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, or the like.

As explained in further detail below, a medical device according to one embodiment of the present invention includes an overlapping configuration including a plurality of overlapping layers of occlusive material. The plurality of layers are configured to be separated into a non-overlapping configuration for delivery within a catheter and return to the overlapping configuration when deployed from the catheter.

According to one embodiment of the present invention for forming a medical device of the invention, the device includes a braided fabric formed of a plurality of wire strands having a predetermined relative orientation with respect to one another. Moreover, the device may comprise a plurality of layers of occluding material such that the device may be a variety of occluding materials capable of at least partially inhibiting blood flow therethrough in order to facilitate the formation of thrombus and epithelialization around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the target site could be assessed using various ultrasound echo doppler modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials other than Nitinol that have elastic properties, such as spring stainless steel, trade named alloys such as Elgiloy, Hastalloy, Phynox, MP35N, or CoCrMo alloys. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One may solder, braze, weld, coat, glue, clamp, tie or otherwise affix the ends of the desired length together. According to one embodiment, each layer of the device may comprise 36-144 wire strands ranging in diameter from about 0.001 to 0.006 in. formed of a shape memory alloy, such as Nitinol, that are braided so as to define fenestrations with an area of about 0.00015 to 0.015 sq. in., which are sufficiently small so as to slow the blood flow through the wall of the device and to facilitate thrombus formation thereon. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its shape in a deformed state. As explained in further detail below in conjunction with the illustrated embodiments, different configurations of devices may be formed and heat set for various locations within the body.

Those skilled in the art will appreciate that in order to speed up the occlusion of the vessel device, the device may be coated with a suitable thrombogenic agent, filled with a polyester fiber, or braided with an increased number of wire strands. The interwoven fiber may attach to a clot to retain the clot firmly within the device as it forms the occlusion.

The device may include a plurality of planes of occlusion. A plane of occlusion may be any surface, whether flat or irregular in shape, that may be oriented at least partially transverse to the flow of blood so as to facilitate the formation of thrombus. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent (or even within) the shunt of an abnormal opening in the patient's organ for example.

The delivery device (not shown) can take any suitable shape, such as an elongate flexible metal shaft or hypotube or metal braided polymer tube configured to constrain the medical device. The device may include no clamps or one or more clamps for engagement with the delivery device. For example, the delivery device may include a threaded distal end for engagement with a threaded bore formed in the clamp of the medical device. The delivery device can be used to urge the medical device through the lumen of a catheter/sheath for deployment in a channel of a patient's body. When the medical device is deployed out the distal end of the catheter, the delivery device still will retain it. Once the medical device is properly positioned within the shunt of the abnormal opening, the shaft of the delivery device can be rotated about its axis to unscrew the medical device from the delivery device. As also explained in further detail below, the specific delivery method will depend on the particular device to be deployed within the body.

In one embodiment the occluder device, the delivery catheter and catheter/sheath accommodate a coaxial guidewire that slideably passes through the device, end clamp(s) and delivery catheter central lumen, and therefore helps guide the delivery device and outer catheter/sheath to the desired location. The guidewire may be delivered independently through the vasculature and across the targeted treatment location or may be extended partially distal to the distal end of the delivery device and catheter/sheath and advanced with the delivery device and catheter/sheath while the guidewire is manipulated to guide the occluder to the desired location. In another embodiment, the catheter/sheath is steerable to assist in placement of the delivery device and occluder. For further discussion regarding a delivery device and methods that may be used to deploy a device according to various aspects of the present invention, see U.S. patent application Ser. No. 11/966,397, which is hereby incorporated in its entirety by reference.

In another embodiment, the device does not have end clamps and the delivery device engages the wire ends at the proximal end of the device between a sleeve and a bead. The sleeve may be connected to a hollow shaft, and the bead may be connected to a cable or wire that passes through the shaft. Relative movement between the bead and the sleeve either engages or releases the braid wire ends at the proximal end of the device. When the wire ends are engaged the delivery device can control the advancement of the device through the delivery catheter. For a further exemplary discussion regarding this delivery device as well as an over the wire version of it, see U.S. Patent Appl. Publ. No. 2007/0118207 to Amplatz et. al., which is hereby incorporated in its entirety by reference.

By keeping the medical device attached to the delivery device, the operator can retract the device for repositioning relative to the abnormal opening, if it is determined that the device is not properly positioned. A delivery device attached to the medical device may allow the operator to control the manner in which the medical device is deployed out the distal end of the catheter. When the medical device exits the catheter, it will tend to resiliently return to a preset, expanded shape, which is set when the fabric is heat-treated. When the device self expands and springs back into this shape, it may tend to act against the distal end of the catheter effectively urging itself forward beyond the end of the catheter. This spring action could conceivably result in improper positioning of the device if the location of the device within the body is critical, such as where it is being positioned in a shunt between two vessels. Since the delivery device can enable the operator to maintain a hold on the device during deployment, the spring action of the device can be controlled by the operator to ensure proper positioning during deployment.

The medical device can be constrained into its reduced diameter configuration and inserted into the lumen of the catheter. According to one embodiment, the medical device may be constrained to an outer diameter of less than about 11 French for delivery within a catheter in the non-overlapping configuration. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g. by manually grasping the ends of the device and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently occlude a channel in the patient's body, one can simply retract the catheter and remove it from the patient's body. This will leave the medical device deployed in the patient's vascular system so that it may occlude the target site, such as a blood vessel or other channel in the patient's body. In some circumstances, the medical device may be attached to a delivery system in such a manner as to secure the device to the end of the delivery device. Before removing the catheter in such a system, it may be necessary to detach the medical device from the delivery device before removing the catheter and the delivery device.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the opening in which it is to be deployed. For instance, the outer diameter of the device may be about 10-30% larger than the inner diameter of the opening. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat and retain the device therein.

When the device is deployed in a patient, thrombi will tend to collect on the surface of the strands. By having a greater strand density and smaller flow passages between strands as afforded by the multiple layer construction of the present invention, the total surface area of the strands and flow resistance will be increased, increasing the thrombotic activity of the device and permitting it to relatively rapidly occlude the vessel in which it is deployed. The device may be delivered and properly placed using two dimensional ICE, MRI, transesophageal echocardiograpy, angiography, and/or Doppler color flow mapping. With the advent of two dimensional ICE, MRI, trans-esophageal echocardiography, bi-plane angiography, and Doppler color flow mapping, the approximate anatomy of the defect can be visualized. The device that is employed will be based on the approximate size of the vessel or abnormality in which the device is to be placed.

Figure 2:
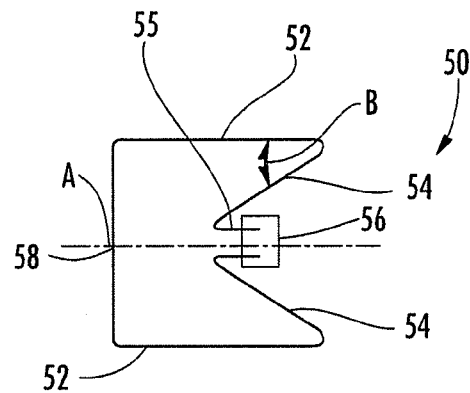

Referring now to the drawings, a discussion of the embodiments of various medical devices of the present invention will next be presented. For example, FIGS. 1-10 illustrate various embodiments of the present invention wherein the medical device 50 is an occluder. For instance, the medical device 50 or variations there of could be used for treating an Arterial Venous Malformation (AVM), an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. With reference to FIG. 1, the medical device 50 comprises an occlusive material in an overlapping configuration having at least three overlapping layers 52, 54, 55. The medical device 50 shown in FIG. 1 has an E-shaped cross section such that the medical device has layers 54, 55 inverted within a cylindrical outer layer 52. A distal end 58 of the medical device 50 is open ended, and the cylindrical outer layer 52 may retain the device in position by engaging the wall of a body lumen. Thus, the proximal end of the medical device 50 may include a cylindrical cavity defined by the overlapping layers 52, 54, 55. The layers 52, 54, 55 may be parallel or substantially parallel to one another. However, the layers 52, 54, 55 may be oriented at various angles with respect to one another. For instance, FIG. 2 shows that the layer 54 may extend obliquely at an angle "B" with respect to the layers 52, 55 or central axis A. As such, the proximal end of the medical device 50 of FIG. 2 defines a frustroconical-shaped cavity.

Figure 10:
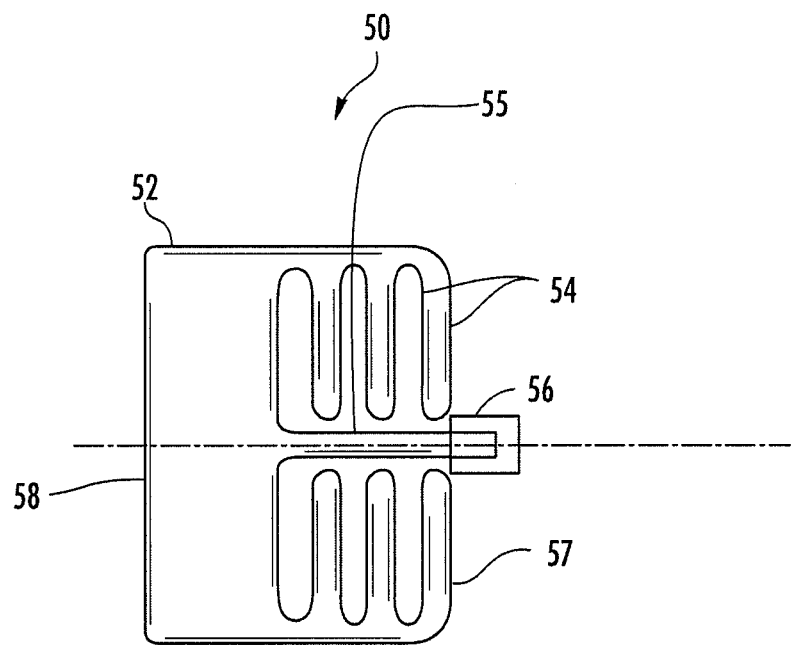

The ends of the occlusive material may be secured with a clamp member 56 or other techniques to secure the ends as described above. For instance, the clamp member 56 could be threadably engaged with a delivery device for delivery within the body and subsequently detached to deploy the medical device 50. As also described above, the medical device 50 may be axially elongated to separate the layers 52, 54, 55 from the overlapping configuration so that the medical device may be delivered within a catheter in a non-overlapping configuration. Thus, the clamp 56 and distal end 58 could be pulled away from one another such that layers 54, 55 are reverted back to an unfolded, non-overlapping configuration. The layers 52, 54, 55 may be unfolded such that the layers are parallel or substantially parallel for delivery within a catheter. An alternative to FIGS. 1 and 2 is shown in FIG. 10 wherein the device 50 has an outer cylindrical layer 52 at end 57 which is bent 90 degrees to form end wall layer 54 and multiple inverted layers 54 parallel to each other and perpendicular to the outer cylindrical layer 52. Each of the inverted layers 54 is a plane of occlusion.

Figure 3:
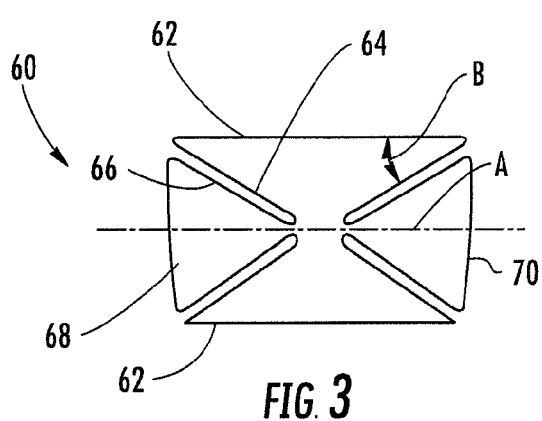

FIG. 3 shows an additional embodiment of the present invention where the medical device 60 is an occluder. The medical device 60 includes a cylindrical outer surface 62 and a pair of surfaces 64, 66 extending obliquely therefrom at an angle "B" and inwardly from each of the proximal 68 and distal 70 ends. Thus, the medical device 60 includes at least three overlapping layers 62, 64, 66 in an overlapping configuration. Moreover, the layers 64 and 66 define respective planes of occlusion in the overlapping configuration with respect to blood flow along the axis extending between the ends 68 and 70.

Figure 4:
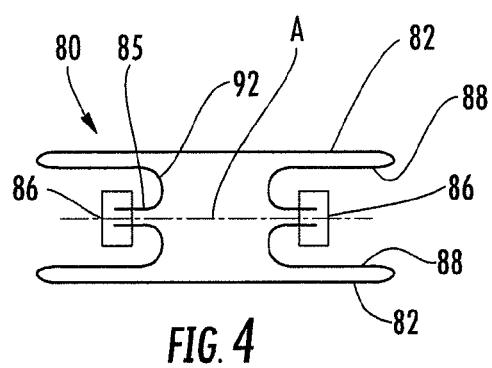

Furthermore, FIG. 4 illustrates a further embodiment of a medical device that may function as an occluder. The medical device 80 shown in FIG. 4 is similar to that of FIG. 1. However, the medical device 80 includes a pair of cylindrical shaped cavities at the proximal and distal ends of the device. In addition, the medical device 80 includes a layer of occlusive material that is heat set and clamped together at its free ends with clamp members 86 such that the device defines a cylindrical outer surface. The medical device 80 includes layer 88 folded inwardly to overlap outer layer 82. Layers 82 and 88 overlap a third layer 85. Curved transitions 92 extend between layers 85, 88, and the ends of the medical device 80 are secured with respective clamping members 86. The clamp members 86 could be pulled away from one another to unfold the layers 82, 85, 88 for delivery within a catheter in a single layer.

Figure 5:
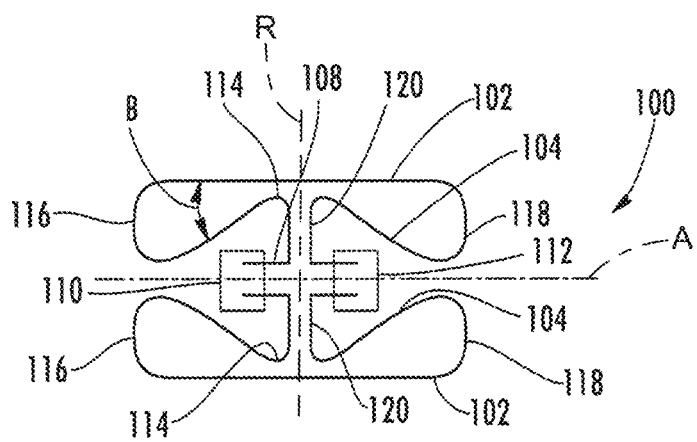

FIG. 5 illustrates an additional embodiment of a medical device 100 or occluder. The medical device 100 is similar to the medical device 80 shown in FIG. 4 in that the free ends 108 of a layer of material are joined by clamp members 110, 112, but the medical device 100 includes a more complex configuration. Namely, the medical device 100 includes overlapping layers 102, 104, where the layer 102 defines a cylindrical outer surface. The layer 104 extends obliquely at an angle "B" with respect to the outer layer 102, and the layers 102, 104 are inverted greater than about 180 degrees with respect to one another. The medical device 100 also includes a proximal curved surface 116 and a distal curved surface 118 that define a curved transition between the overlapping layers at the proximal and distal ends. In addition, the layer 104 extends obliquely and has a curved transition 114 proximate to the outer layer 102. This curved transition 114 is configured to apply an outward force on the outer layer 102. For example, when the medical device 100 is positioned within a body lumen, the curved transition 114 may provide an outward force against the outer layer 102 and the wall of the body lumen, thereby providing additional fixation therein. The medical device 100 also includes planar surfaces 120 extending perpendicular to the central axis A (i.e., along a radial axis R extending perpendicular to central axis A) and between the curved transitions 114 and the clamping members 110, 112, which may provide planes of occlusion when positioned within the vasculature. Additionally, surfaces 116, 118, and 104 act as planes of occlusion.

Figure 6:
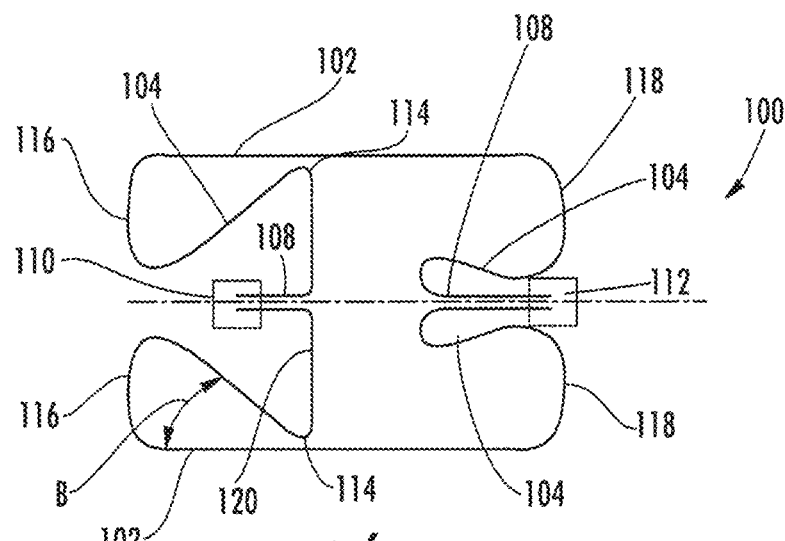

It is understood that the configuration of the medical device 100 shown in FIG. 5 is not meant to be limiting. For example, the angle "B" that the layer 104 extends with respect to the outer layer 102 may vary depending on the target site. According to one aspect, FIG. 6 shows that layer 104 may extend at different oblique angles "B", wherein the layer 104 in FIG. 6 extends at a greater angle than that shown in FIG. 5. Moreover, the configuration of the medical device 100 may vary at the proximal and distal ends. For example, FIG. 6 shows that the layer 104 extends inwardly from a proximal curved surface 116 and forms a curved transition 114 proximate to the outer layer 102. A planar surface 120 also extends between the curved transition 114 and the clamping member 110. The distal end of the medical device 100 has a different configuration, wherein the layer 104 extends slightly towards the outer surface 102 and transitions back to the clamp member 112. Thus, the proximal end of the device 100 shown in FIG. 6 has a more open configuration where the clamp member 110 is located within the recess defined between the overlapping layers 102, 104. At the distal end, the layer 104 overlaps the free ends 108, while the free ends extend distally of the distal curved surfaces 118 to the clamp member 112.

Figure 7:
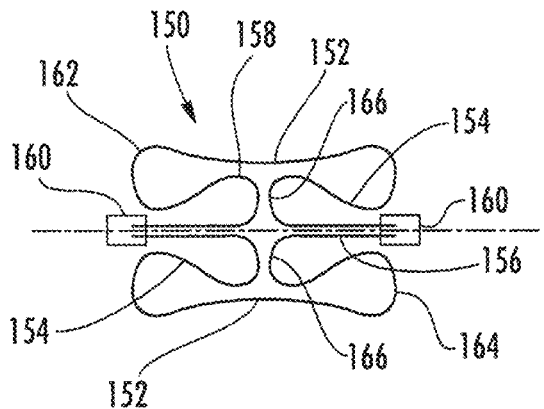

FIG. 7 shows an additional embodiment of a medical device 150 that may function as an occluder. Similar to the embodiments shown in FIGS. 4-6, the medical device 150 includes a single layer of material in an overlapping configuration, with its free ends 156 coupled with a pair of clamping members 160. That is, the medical device 150 includes an outer layer 152 that overlaps inner layer 154. The outer layer 152 has a cylindrical configuration, while the layer 154 extends obliquely with respect to the outer layer and has a curved transition 158 that extends proximate to the outer layer as described above. Rather than a planar surface, the medical device 150 includes curved surfaces 166 extending from the curved transitions 158, with the free ends 156 extending parallel to the outer layer 152 and to the clamping members 160. Thus, the inner layer 154 overlaps the free ends 156 and is also slightly curved. In addition, the medical device 150 includes bulbous regions 162 extending between the outer layer 152 and the inner layer 154 at the proximal and distal ends of the medical device. The bulbous regions 162 thus extend further outwardly in diameter than the cylindrical outer layer 152 and may be configured to engage the wall of a body lumen when deployed therein.

Figure 8:
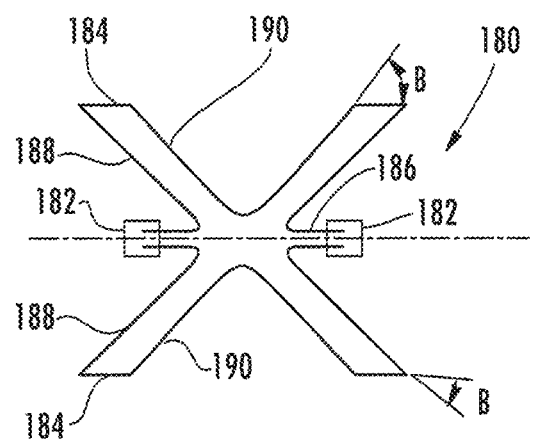

In yet another embodiment of the present invention, a medical device 180 is shown in FIG. 8. The medical device 180 includes an overlapping configuration having a plurality of overlapping layers 184, 186, 188, 190, with the free ends 186 of the device coupled with a pair of clamping members 182. The medical device 180 has an X-shaped cross section, wherein the outer layer 184 defines a cylindrical portion that may be configured to engage the wall of a body lumen. A pair of overlapping layers 188, 190 extend parallel to one another and obliquely at an angle "B" with respect to the outer layer 184. The medical device 180 may include funnel or frustro-conical-shaped recesses at its proximal and distal ends, as well as an annular recess extending within and about the entire circumference of the outer surface 184.

Figure 9:
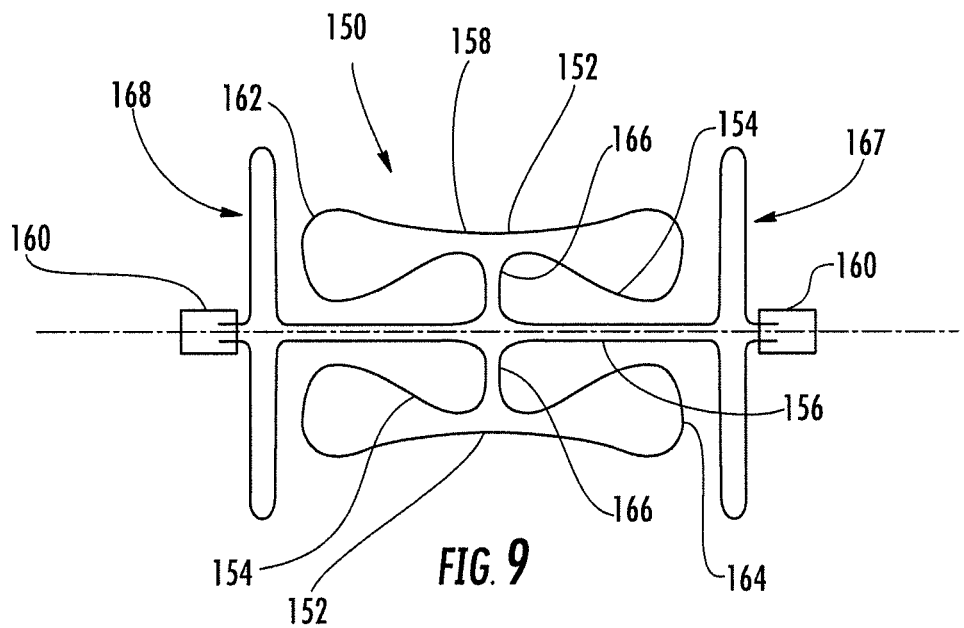

Another embodiment as shown in FIG. 9 is an occluder particularly adapted for septal defect occlusion such as for an ASD, VSD or PDA. The device is similar to that shown in FIG. 7 except for the additional disks 167 and 168 formed from the fabric at the center of each end with the clamps 160 displaced outward from that shown in FIG. 7. The disks 167 and 168 are positioned on either side of the septum to secure the device with the central portion between the disks occluding the defect. The addition of the disks 167, 168 is illustrative of various modifications that may be made to an occluder for adaptability to various anatomical conditions. In addition, only one disk may be added. The disks may have a portion angled or curved such as to form a concave or convex surface. As indicated above, the device 150 shown in FIG. 9 may be elongated for delivery through a catheter as a single layer while forming overlapped layers within the target location when deployed from the catheter.

As indicated above, the overlapping layers of the medical devices may be separated from one another into a non-overlapping configuration for delivery within a catheter. The non-overlapping configuration may have different diameters in different locations and a greater length than the overlapping configuration. Accordingly, because the medical devices may be delivered in a non-overlapping configuration, the medical devices may be delivered within a catheter having a smaller diameter than other multi-layered medical devices that are not capable of being separated. Moreover, the medical devices may include raised or recessed surfaces or similar irregularities, which may correspond to heat set, inversion points. These surface irregularities may be felt during delivery of the device as they pass through the delivery catheter tip and may serve as a means of tactile feedback to alert the operator of the stage of device delivery even without visualization by other means.

Various techniques could be employed to fabricate the medical devices. According to one embodiment, the medical devices are formed from a single layer of occlusive material. For instance, the medical devices may be braided to form a tubular fabric made of an elastic or shape memory metallic material such as Nitinol. The medical devices may be inverted to form a plurality of overlapping layers and then heat set in a mold or by placing a mandrel in the inside to maintain the desired inside shape. For example, one end of the medical devices may be pushed distally inside itself to form two or more overlapping layers. When the desired overlapping configuration is obtained, the medical device would then be heated in a mold to a predetermined temperature and for a length of time sufficient to heat set the overlapping layers. Thus, when the medical devices are forced from the overlapping configuration to the non-overlapping configuration, the layers return to the overlapping configuration when the force is removed.

In use, the medical devices would be delivered at a diameter that is smaller than its heat set diameter. Typically, the medical devices would be constrained, such as by axially elongating the medical devices to a smaller diameter and positioning the distal end of the fabric wires within a delivery catheter for delivery to a target site. For those medical devices having a clamp member at its proximal end, the clamp member may be engaged by a delivery device, such as by threadable engagement, and inserted within a delivery catheter. When the medical device is deployed out the distal end of the catheter, the device will still be retained by the delivery device. Once the proper position of the medical device in the vessel, body organ, or the like is confirmed, the shaft of the delivery device may be rotated about its axis to unscrew the clamp member from the threaded end of the delivery device. Of course, the threaded connection could be at either end of the medical device depending on the anatomical situation and the desired or available means of access to the treatment site.

By keeping the medical device attached to the delivery system, the operator may still retract the medical device back into the delivery catheter for repositioning if it is determined that the medical device is not properly positioned in the first attempt. In instances where the medical device is improperly deployed on a first try, the device may be recovered by pulling the delivery device proximally, thereby retracting the medical device back into the delivery catheter prior to a second attempt at positioning the medical device relative to the vessel, body organ, or the like. The threaded attachment may also allow the operator to control the manner in which the medical device is deployed out of the distal end of the delivery catheter. As explained below, when the medical device exits the delivery catheter it will tend to resiliently return to an expanded shape which was set when the fabric was heat treated. When the device springs back into this shape, it may tend to act against the distal end of the catheter, effectively urging itself forward beyond the end of the catheter. This spring action could conceivably result in improper positioning of the device. Since the threaded clamp member can enable the operator to maintain a hold on the device during deployment, the spring action of the device can be controlled and the operator can control the deployment to ensure proper positioning.

For those medical devices having one clamp member (e.g., FIGS. 1 and 2) or those not having a clamp member (e.g., FIG. 3), a funnel shaped introducer device may be employed to facilitate the insertion of the device by having the distal end of the funnel inserted into the delivery catheter proximal end lumen and advancing the braid end into the lumen. Alternatively the delivery device may be inserted through the delivery catheter lumen, exiting the distal end of the catheter and attached to the proximal end of the device end connector or fabric end, and the device pulled proximally into the delivery catheter lumen.

In either case, the delivery device may be releasably attached to the medical device prior to insertion into the delivery catheter. The delivery catheter, medical device, and delivery device, would be introduced into the patient together, through an introducer sheath and placed using the Seldinger technique to gain vascular access such as through the femoral artery. The medical device would then be guided through the vascular system until a distal end of the delivery catheter is proximate to a target site to be treated, such as within a lumen. With the medical device and the delivery device held stationary, the delivery catheter is withdrawn in the proximal direction to partially eject the medical device from the distal end of the delivery catheter until a distal portion of the medical device then self-expands to engage the lumen. The natural tendency of the medical device is to return to the expanded overlapping and heat set configuration once released from the catheter, although some intervention by the physician may be necessary in order for the medical device to return to the overlapping heat set configuration and be fully deployed. For example, once a portion of the medical device is deployed, the physician may need to urge the delivery device and or delivery catheter distally so as to force the medical device to invert within itself to initially begin the formation of overlapping layers. To fully deploy the medical device, the physician may need to further retract the delivery catheter while advancing the delivery device until either visual or tactile feedback indicates that one or more layers have been fully deployed. Distal advancement of the delivery device and/or proximal retraction of the delivery catheter may result in deploying additional overlapping layers as the layers return to their inverted heat set configuration. When the medical device is fully deployed from the delivery catheter, the clamp member may be actuated to release the proximal end of the medical device. For further exemplary details regarding a delivery catheter, a delivery device, clamp member, and over-the-wire delivery, and methods of using the same, Applicants hereby incorporate U.S. Patent Appl. Publ. No. 2006/0253184, filed May 4, 2005 and U.S. Patent Appl. Publ. No. 2007/0118207A1, filed Jan. 17, 2007, herein in their entirety.

In an alternative technique for delivering a medical device, a guide wire may be inserted through an introducer sheath and advanced to the treatment site. A delivery catheter may then be introduced over the guide wire and tracked to the treatment site. The medical device attached proximally to the delivery device may then be introduced over the guide wire or alternatively the guide wire removed. The distal end of the device may be loaded into the funnel introducer and fed into the proximal lumen of the delivery catheter and advanced using the delivery device to place the distal end of the device near the distal end of the delivery catheter. The medical device may then be deployed as previously described above.

As described above, the specific technique used to deliver a medical device may vary based on the type of medical device and where the device is being deployed. With respect to the embodiments shown in FIGS. 1-10, wherein the medical device may be an occluder, the devices may include no clamps or one or more clamps for securing the ends of the material and engaging a delivery device, such as via threadable engagement. For example, FIGS. 1, 2, and 10 show medical devices having one clamp member, while FIGS. 4-9 show both the proximal and distal ends having a clamp member, wherein one of the clamp members may be configured to engage a delivery device, typically at the proximal end of the medical device. Similarly, the proximal end of the medical devices shown in FIGS. 3 and 11 may be engaged by a delivery device having a locking member configured to lock onto the proximal end circumference of the medical device. Thus, the clamp members securing the free ends of the medical device and the locking member of the delivery device may be used to engage the proximal and distal ends and pull the ends of the medical device apart so as to separate the overlapping layers of material into a single layer of material for delivery within a catheter. Although the medical device embodiments shown in FIGS. 1-11, may be configured to spring back to the expanded heat set configuration when deployed from the delivery catheter, further user intervention, may be necessary in some instances in order to facilitate folding of the material into overlapping layers. This may be particularly true at the point of inversion from outer layer to first inverted inner layer where the fabric is somewhat resistant due to an over-center condition in which the outer diameter of the outside layer proximal end must be expanded a small amount to allow for the inversion to occur.

Moreover, each of the overlapping layers of the embodiments shown in FIGS. 1-9 may be aligned with the central axis within about 45 degrees or less. For example, FIG. 1 shows layers 52, 54, 55 that are substantially parallel to the central axis A, while FIG. 2 shows that layers 52, 55 extend parallel to the central axis A and layer 54 extends obliquely (e.g., about 45 degrees) with respect to the central axis A. Similarly, the overlapping layers may be inverted at various angles with respect to one another. For instance, FIG. 2 shows that layer 54 is inverted less than about 180 degrees with respect to layer 52, while FIGS. 5 and 6 show layers 102, 104 inverted greater than about 180 degrees with respect to one another. Furthermore, the layers may overlap along various lengths of one another. For instance, one layer may overlap at least 50% of another overlapping layer. FIG. 1 shows that layer 52 may completely overlap the length of layers 54, 56, while FIG. 9 shows that layer 152 may overlap layer 154 and a substantial portion of layer 156. Accordingly, various modifications may be made to the medical devices for adaptability to various anatomical conditions.

Embodiments of the present invention may provide several advantages. For example, a medical device having a plurality of overlapping layers may be separated into a single layer for delivery within a catheter. Thus, the medical device may be delivered within a catheter having a smaller inner diameter than multi-layered medical devices that may not otherwise be capable of being separated into a single layer. Therefore, the medical device may provide the benefits of a multi-layered device after deployment while providing the benefits of a single-layered device prior to deployment. As such, the device may be capable of being delivered to harder to access locations within the body, as well as be delivered through smaller diameter vessels, openings, cavities, and the like. Moreover, the medical device may be used to occlude, shunt, restrict flow in vessels, channels, lumens, cavities, or organs anywhere in the vasculature or body.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An occlusion device for occluding a target site, the device comprising:
   an occlusive material comprising a tubular fabric having proximal and distal ends and a central axis extending therebetween, each of the proximal and distal ends being secured at a point along the central axis such that the tubular fabric is configured to at least partially inhibit blood flow between the proximal and distal ends, the occlusive material having a preset, overlapping configuration comprising at least three overlapping layers folded over each other by inversion such that the at least three overlapping layers overlap one another along the central axis and such that substantially an entire length of an innermost layer of the at least three overlapping layers and substantially an entire length of an outermost layer of the at least three overlapping layers are spaced apart from one another along a radial axis that is perpendicular to the central axis, wherein the at least three overlapping layers are aligned with the central axis within about 45 degrees or less and are configured to be separated and disposed within a catheter in a non-overlapping configuration and to at least partially return to the preset, overlapping configuration when deployed from the catheter and wherein at least one pair of the at least three overlapping layers that are directly next to each other are folded greater than 180 degrees with respect to one another in the preset, overlapping configuration, one of the at least three overlapping layers having a free end secured at the proximal or distal end such that a remaining unsecured portion of the layer extending from the free end defines an outer surface configured to be exposed to blood flow at the target site.

2. The occlusion device of claim 1, wherein the occlusive material comprises a plurality of strands braided into a continuous layer of tubular fabric.

3. The occlusion device of claim 2, wherein the tubular fabric comprises braided strands of a shape memory alloy, each metal strand having a pair of free ends.

4. The occlusion device of claim 3, further comprising at least one clamp configured to secure a free end of each of the braided metal strands.

5. The occlusion device of claim 4, wherein the device has a proximal end and a distal end and the at least one clamp is located distally with respect to the proximal end of the device or proximally with respect to the distal end of the device in the preset, overlapping configuration.

6. The occlusion device of claim 4, wherein the at least one clamp further comprises a pair of clamps, each clamp configured to secure respective free ends of the braided metal strands.

7. The occlusion device of claim 6, wherein at least a portion of each overlapping layer is located exteriorly of each of the pair of clamps.

8. The occlusion device of claim 4, wherein at least a portion of each overlapping layer is located exteriorly of the at least one clamp.

9. The occlusion device of claim 1, wherein the occlusive material further comprises a plurality of layers extending perpendicularly to the central axis in the preset, overlapping configuration.

10. The occlusion device of claim 1, wherein the occlusive material is configured to be axially elongated to separate the at least three overlapping layers into the non-overlapping configuration.

11. The occlusion device of claim 1, wherein the occlusive material comprises an inner surface and an outer surface in the non-overlapping configuration, and wherein at least a portion of the occlusive material is configured to fold over itself such that a portion of the outer surface overlies another portion of the outer surface.

12. The occlusion device of claim 1, wherein at least one overlapping layer overlaps at least 50% of another overlapping layer.

13. The occlusion device of claim 1, wherein at least a pair of the at least three overlapping layers include surface portions that are configured to be substantially parallel to one another and the central axis in the preset, overlapping configuration.

14. The occlusion device of claim 1, wherein the occlusive material is configured to be constrained to an outer diameter of less than about 11 French for delivery within a catheter in the non-overlapping configuration.

15. The occlusion device of claim 1, wherein a portion of at least one of the three overlapping layers of the occlusive material comprises a cylindrical outer surface extending parallel to the central axis in the preset, overlapping configuration.

16. The occlusion device of claim 15, wherein a portion of one of the at least three overlapping layers comprises a surface extending obliquely with respect to the central axis and within the cylindrical outer surface.

17. The occlusion device of claim 16, wherein a portion of the oblique surface is curved.

18. The occlusion device of claim 16, wherein a portion of the oblique surface is configured to abut the cylindrical outer surface.

19. The occlusion device of claim 1, wherein a cross-section of the occlusive material is symmetrical about an axis extending perpendicular to the central axis in the preset, overlapping configuration.

20. The occlusion device of claim 1, wherein a cross-section of the occlusive material is symmetrical about an axis extending perpendicular to the central axis in the preset, overlapping configuration.

* * * * *